(12) United States Patent
Wei et al.

(10) Patent No.: US 9,114,087 B2
(45) Date of Patent: Aug. 25, 2015

(54) PROCESS FOR MAKING VISUALLY DISTINCTIVE MULTIPLE LIQUID PHASE COMPOSITIONS

(75) Inventors: Karl Shiqing Wei, Mason, OH (US); Bryce William Wilson, Hamilton, OH (US); John Eric VanHook, II, Cincinnati, OH (US); Andrés Ernesto Velarde, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 2600 days.

(21) Appl. No.: 10/837,214

(22) Filed: Apr. 30, 2004

(65) Prior Publication Data

US 2004/0219119 A1     Nov. 4, 2004

Related U.S. Application Data

(60) Provisional application No. 60/473,692, filed on Jul. 16, 2003, provisional application No. 60/467,180, filed on May 1, 2003.

(51) Int. Cl.
| | | |
|---|---|---|
| *B65B 1/04* | (2006.01) | |
| *A61K 8/31* | (2006.01) | |
| *A61Q 19/00* | (2006.01) | |

(Continued)

(52) U.S. Cl.
CPC ... *A61K 8/31* (2013.01); *A61K 8/03* (2013.01); *A61Q 19/00* (2013.01); *A61Q 19/10* (2013.01); *A61K 2800/87* (2013.01)

(58) Field of Classification Search
USPC ............ 141/2, 9, 105, 268; 222/145.3, 145.1; 137/602
See application file for complete search history.

(56) References Cited

U.S. PATENT DOCUMENTS

| 2,020,454 A | 11/1935 | Bisbee et al. |
| 2,658,072 A | 11/1953 | Kosmin |

(Continued)

FOREIGN PATENT DOCUMENTS

| CA | 2246316 | 6/1998 |
| DE | 19650952 A | 6/1998 |

(Continued)

OTHER PUBLICATIONS

XP 002332778 "Dove All Day Moisturizing Body Wash" Online URL: http://www.ewg.org/reprots/skindeep/productinfo.php?prod_id=901910.

(Continued)

*Primary Examiner* — Jason K Niesz

(57) ABSTRACT

A process for making multi-phase liquid compositions is disclosed. For example, a plurality of liquid phases can be placed in separate vessels equipped with supply lines. Predetermined amounts of each of the liquid phase can be transferred, via the supply lines, into a combiner that aligns each of the liquid phases. The liquid phases can be transferred from the combiner to a blender. A mixing element of the blender can blend the liquid phases together to produce a multi-phase liquid composition having a visually distinct pattern formed by the liquid phases. The multi-phase liquid phase composition can be transferred to an individual product container via a delivery nozzle. When said multi-phase liquid composition is transferred to said individual product container via said delivery nozzle, the individual product container can be rotated, via a rotating platform of a bottle holding device.

20 Claims, 3 Drawing Sheets

(51) Int. Cl.
*A61Q 19/10* (2006.01)
*A61K 8/03* (2006.01)

(56) References Cited

U.S. PATENT DOCUMENTS

| | | | |
|---|---|---|---|
| 2,986,271 A | 5/1961 | Forrer | |
| 3,455,440 A | 7/1969 | West | |
| 3,479,429 A | 11/1969 | Morshauser et al. | |
| 3,533,955 A | 10/1970 | Pader et al. | |
| 3,542,256 A | 11/1970 | Waterman | |
| 3,618,757 A | 11/1971 | Funkhouser | |
| 3,800,998 A | 4/1974 | Gask | |
| 3,850,365 A | 11/1974 | Dietrich | |
| 3,899,076 A | 8/1975 | Florian | |
| 3,929,678 A | 12/1975 | Laughlin et al. | |
| 3,937,811 A | 2/1976 | Papantoniou et al. | |
| 3,951,679 A | 4/1976 | Bernhard et al. | |
| 3,980,767 A | 9/1976 | Chown et al. | |
| 4,159,028 A | 6/1979 | Barker et al. | |
| 4,263,363 A | 4/1981 | Buck et al. | |
| 4,335,103 A | 6/1982 | Barker et al. | |
| 4,379,753 A | 4/1983 | Bolich, Jr. | |
| 4,425,322 A | 1/1984 | Harvey et al. | |
| 4,518,578 A | 5/1985 | Hayes et al. | |
| D292,879 S | 11/1987 | Smith | |
| 4,818,575 A * | 4/1989 | Hirata et al. | 428/36.7 |
| 4,966,205 A | 10/1990 | Tanaka | |
| 4,980,155 A | 12/1990 | Shah et al. | |
| 5,002,680 A | 3/1991 | Schmidt et al. | |
| 5,059,414 A | 10/1991 | Dallal et al. | |
| 5,223,315 A | 6/1993 | Katsura et al. | |
| 5,228,189 A | 7/1993 | Driller et al. | |
| 5,304,334 A | 4/1994 | Lahanas et al. | |
| 5,393,450 A | 2/1995 | Shana'a et al. | |
| 5,455,035 A | 10/1995 | Guerrero et al. | |
| 5,487,168 A | 1/1996 | Geiner et al. | |
| 5,540,853 A | 7/1996 | Trinh et al. | |
| 5,556,628 A | 9/1996 | Derian et al. | |
| 5,578,299 A | 11/1996 | Starch | |
| 5,612,307 A | 3/1997 | Chambers et al. | |
| 5,632,420 A | 5/1997 | Lohrman et al. | |
| 5,635,171 A | 6/1997 | Nadaud et al. | |
| 5,661,189 A | 8/1997 | Grieveson et al. | |
| 5,687,779 A * | 11/1997 | Andersson et al. | 141/105 |
| 5,716,920 A | 2/1998 | Glenn et al. | |
| 5,851,978 A | 12/1998 | Shana'a | |
| 5,873,494 A | 2/1999 | Dallas, Jr. | |
| 5,925,603 A | 7/1999 | D'Angelo | |
| 5,929,019 A | 7/1999 | Puvvada et al. | |
| 5,947,335 A | 9/1999 | Milio et al. | |
| 5,952,286 A | 9/1999 | Puvvada et al. | |
| 5,954,213 A | 9/1999 | Gerhart et al. | |
| 5,965,500 A | 10/1999 | Puvvada | |
| 5,965,501 A | 10/1999 | Rattinger et al. | |
| 5,972,361 A | 10/1999 | Fowler et al. | |
| D426,158 S | 6/2000 | Flurer et al. | |
| 6,174,845 B1 | 1/2001 | Rattinger et al. | |
| 6,176,391 B1 | 1/2001 | Rehkemper et al. | |
| 6,176,395 B1 | 1/2001 | Abbott et al. | |
| 6,190,648 B1 | 2/2001 | Kouzu et al. | |
| 6,194,364 B1 | 2/2001 | Glenn, Jr. | |
| D438,460 S | 3/2001 | Hammond | |
| D439,165 S | 3/2001 | Erckelbout et al. | |
| 6,213,166 B1 | 4/2001 | Thibiant et al. | |
| D441,645 S | 5/2001 | Longhurst | |
| 6,232,496 B1 | 5/2001 | Carr et al. | |
| 6,245,323 B1 | 6/2001 | Christie et al. | |
| 6,245,344 B1 | 6/2001 | Thibiant et al. | |
| 6,268,322 B1 | 7/2001 | St. Lewis et al. | |
| 6,306,806 B1 | 10/2001 | St. Lewis et al. | |
| 6,335,312 B1 | 1/2002 | Coffindaffer et al. | |
| 6,340,723 B1 | 1/2002 | Nitta et al. | |
| D455,655 S | 4/2002 | Bunce | |
| 6,367,519 B2 | 4/2002 | Thibiant et al. | |
| 6,383,999 B1 | 5/2002 | Coyle et al. | |
| 6,385,992 B1 | 5/2002 | Flore, Jr. | |
| 6,394,323 B2 | 5/2002 | McClean et al. | |
| 6,419,783 B1 | 7/2002 | Rainey et al. | |
| 6,426,326 B1 | 7/2002 | Mitra et al. | |
| 6,429,177 B1 | 8/2002 | Williams et al. | |
| 6,495,498 B2 | 12/2002 | Niemiec et al. | |
| 6,506,391 B1 | 1/2003 | Biatry | |
| 6,517,939 B1 | 2/2003 | Moini et al. | |
| 6,521,216 B1 | 2/2003 | Glandorf et al. | |
| 6,534,456 B2 | 3/2003 | Hayward et al. | |
| 6,534,457 B2 | 3/2003 | Mitra | |
| 6,547,063 B1 | 4/2003 | Zaveri et al. | |
| 6,555,509 B2 | 4/2003 | Abbas et al. | |
| 6,564,978 B1 | 5/2003 | Safian et al. | |
| 6,574,985 B2 | 6/2003 | Fiore, Jr. | |
| 6,589,509 B2 | 7/2003 | Keller et al. | |
| 6,652,134 B2 | 11/2003 | Lloyd | |
| 6,663,855 B2 | 12/2003 | Frechet | |
| 6,673,371 B2 | 1/2004 | Brown et al. | |
| 6,673,755 B2 | 1/2004 | Wei et al. | |
| D486,395 S | 2/2004 | Lovell et al. | |
| D486,398 S | 2/2004 | Lovell et al. | |
| 6,691,394 B1 | 2/2004 | McClean | |
| 6,695,510 B1 | 2/2004 | Look et al. | |
| 6,729,501 B2 | 5/2004 | Peterson | |
| 6,924,256 B2 | 8/2005 | Massaro et al. | |
| 7,143,893 B2 | 12/2006 | Kelly | |
| 7,144,542 B2 | 12/2006 | Holzer et al. | |
| 7,273,837 B2 | 9/2007 | Boutique et al. | |
| 7,511,003 B2 | 3/2009 | Focht et al. | |
| 7,524,807 B2 | 4/2009 | Clapp et al. | |
| 7,537,819 B2 | 5/2009 | Hendricks | |
| 7,666,825 B2 | 2/2010 | Wagner et al. | |
| 2001/0035230 A1 | 11/2001 | Thibiant | |
| 2001/0036467 A1 | 11/2001 | Thibiant et al. | |
| 2002/0004468 A1 | 1/2002 | Hodge et al. | |
| 2002/0010110 A1 | 1/2002 | Hayward et al. | |
| 2003/0003069 A1 | 1/2003 | Carson et al. | |
| 2003/0152540 A1 | 8/2003 | Putman et al. | |
| 2003/0161852 A1 | 8/2003 | Miller et al. | |
| 2003/0180246 A1 | 9/2003 | Frantz et al. | |
| 2003/0222100 A1 | 12/2003 | Husband et al. | |
| 2004/0048757 A1 | 3/2004 | Zhang et al. | |
| 2004/0048758 A1 | 3/2004 | Zhang et al. | |
| 2004/0057920 A1 | 3/2004 | Focht et al. | |
| 2004/0091445 A1 | 5/2004 | Dykstra et al. | |
| 2004/0105827 A1 | 6/2004 | Grimm et al. | |
| 2004/0146475 A1 | 7/2004 | Peffly et al. | |
| 2004/0158940 A1 | 8/2004 | Wells et al. | |
| 2004/0180020 A1 | 9/2004 | Manelski et al. | |
| 2004/0219119 A1 | 11/2004 | Wei et al. | |
| 2004/0223929 A1 | 11/2004 | Clapp et al. | |
| 2004/0223991 A1 | 11/2004 | Wei et al. | |
| 2004/0232023 A1 | 11/2004 | Bansal et al. | |
| 2004/0235693 A1 | 11/2004 | Wei et al. | |
| 2004/0242706 A1 | 12/2004 | Wiersema et al. | |
| 2004/0248748 A1 | 12/2004 | Wei et al. | |
| 2004/0248749 A1 | 12/2004 | Mitra et al. | |
| 2005/0003975 A1 | 1/2005 | Browne et al. | |
| 2005/0020468 A1 | 1/2005 | Frantz et al. | |
| 2005/0100570 A1 | 5/2005 | Wei et al. | |
| 2005/0139574 A1 | 6/2005 | Simone et al. | |
| 2005/0143269 A1 | 6/2005 | Wei et al. | |
| 2005/0192187 A1 | 9/2005 | Wagner et al. | |
| 2005/0192188 A1 | 9/2005 | Wagner et al. | |
| 2005/0192189 A1 | 9/2005 | Wagner et al. | |
| 2005/0238680 A1 | 10/2005 | Stella et al. | |
| 2005/0249758 A1 | 11/2005 | Di Puccio Pagano | |
| 2005/0269372 A1 | 12/2005 | Smith | |
| 2005/0276768 A1 | 12/2005 | Wei et al. | |
| 2006/0002880 A1 | 1/2006 | Peffly et al. | |
| 2006/0008438 A1 | 1/2006 | Velarde et al. | |
| 2006/0079420 A1 | 4/2006 | Wagner et al. | |
| 2011/0009302 A1 | 1/2011 | Soffin et al. | |

FOREIGN PATENT DOCUMENTS

| | | |
|---|---|---|
| DE | 198 54 086 A | 5/2000 |
| EP | 0 078138 A2 | 5/1983 |

(56) References Cited

FOREIGN PATENT DOCUMENTS

| | | |
|---|---|---|
| EP | 0 331617 B | 4/1992 |
| EP | 1 108421 A2 | 6/2001 |
| EP | 0 907345 B1 | 5/2003 |
| GB | 1277324 A | 6/1972 |
| JP | 2000-229817 A | 8/2000 |
| JP | 2000229817 A | 8/2000 |
| JP | 2002/128639 A | 5/2002 |
| JP | 2002/138010 A | 5/2002 |
| WO | WO 90/13283 A1 | 11/1990 |
| WO | WO 94/10973 A1 | 5/1994 |
| WO | WO 97/17938 A1 | 5/1997 |
| WO | WO 98/27193 A1 | 6/1998 |
| WO | WO 98/33477 | 8/1998 |
| WO | WO 99/38489 A1 | 8/1999 |
| WO | WO 99/38491 A1 | 8/1999 |
| WO | WO 00/75240 A1 | 12/2000 |
| WO | WO 01/01931 A1 | 1/2001 |
| WO | WO 01/23517 A1 | 4/2001 |
| WO | WO 01/70193 A2 | 9/2001 |
| WO | WO 01/70926 A1 | 9/2001 |
| WO | WO 02/100358 A1 | 12/2002 |
| WO | WO 02/100358 A1 | 12/2002 |
| WO | WO 03/055456 A1 | 7/2003 |
| WO | WO 03/105796 A1 | 12/2003 |
| WO | WO 2004/018609 A1 | 3/2004 |
| WO | WO 2004/026276 A1 | 4/2004 |
| WO | WO 2004/050055 A1 | 6/2004 |
| WO | WO 2005/067875 A1 | 7/2005 |

OTHER PUBLICATIONS

XP002332779 "Olay Daily Renewal Moisturizing Body Wash" Online URL: http://householdprdoucts.nlm.nih.gov/cgi-bin/household.brands?tbl=brands&id=16003084.
C.D. Vaughan, "Solubility, Effects in Product, in Package, Penetration and Preservation," Cosmetic and Toiletries, vol. 103, Oct. 1988.
Crank, Mathematics of Duffusion, $2^{nd}$ Edition, p. 63, 1975.
CTFA International Cosmetic Ingredient Dictionary, Fourth Edition, 1991, pp. 12 and 80.
Milton, Introduction to Probability and Statistics, $4^{th}$ Edition p. 317 (Section 9.2: Testing Hypotheses on a Proportion), Sep. 30, 2002.
J. Caelles et al., "Anionic and Cationic Compounds in Mixed Systems," Cosmetics & Toiletries, vol. 106, Apr. 1991. pp. 49-54.
C.J. van Oss, "Coacervation, Complex-Coacervation and Flocculation," J. Dispersion Science and Technology, vol. 9 (5, 6), 1988-89, p. 561-573.
D.J. Burgess, "Practical Analysis of Complex Coacervate Systems," J. of Colloid Anti Interface Science, vol. 140, No. 1, Nov. 1990, pp. 227-238.
Kobo Brochure, "Treated Pigments" (May 2000).

\* cited by examiner

PROCESS FOR MAKING VISUALLY DISTINCTIVE MULTIPLE LIQUID PHASE COMPOSITIONS

CROSS REFERENCE TO RELATED APPLICATION(S)

This application claims the benefit of U.S. Provisional Application No. 60/473,692, filed Jul. 16, 2003, and U.S. Provisional Application No. 60/467,180, filed May 1, 2003.

FIELD OF THE INVENTION

The invention relates to compositions with multiple phases and processes for making such compositions. These compositions are easily dispensed from their containers such that consistent doses of each phase are expelled from the container at each dispensing event.

BACKGROUND OF THE INVENTION

Under the time pressures of daily life, individuals are seeking more efficient ways to address personal hygienic needs. For example, two-in-one shampoos that cleanse and condition in a single step are widely used by the consuming public. This same convenience is sought by consumers in the form of skin cleansing products that clean like bar soap, but also condition the skin. Early attempts at providing such a product employed dual-chamber packaging containing separate cleansing and conditioning products. The separate conditioning and cleansing compositions remain physically separate and stable during prolonged storage. These packages were designed to co-dispense the products together to effectuate simultaneous cleaning and conditioning. In another embodiment, the cleaning and conditioning products are mixed just prior to dispensing. Although such dual-chamber delivery systems seemed to provide improved the convenience sought by consumers, they frequently failed to achieve consistent and uniform performance because of the uneven dispensing of the different phases. Additionally, these packaging systems add considerable cost to the finished product and tended to be obtrusive in areas such as usual home tub/showers.

Alternatively, cleansing cream-astringent compositions comprising a cream phase and a gel phase were combined in typical product packaging for simultaneous dispensing of both phases. These products required special processing wherein two initially separate and distinct phase compositions are channeled to a filling head and simultaneously dispensed into rotating package or container. Stirring the product in the filling head during packaging is achieved by using a plurality of stirring rods disposed about the filling head. Note that these cleansing cream-astringent products do not contain a "surfactant" phase, such as typically found in personal cleansing products. Furthermore, even if such a composition contained a surfactant phase, the individual phases would be unevenly dosed from typical packaging. This would make such cleansing cream-astringent products unsuitable for use as a two-in-one type of personal cleansing products that is sought by the consuming public.

Other attempts to produce multiple liquid phase products that evenly dispense from routine packaging have been produced by providing two compounds in separate storage vessels and dedicated pumps wherein each phase is introduced through separate nozzles into a rotating package. These products typically have at least one colored phase, and only contain material such as surfactants. Since the compositions only contain surfactants, these compositions comprise no separate skin conditioning phase that comprises relatively high lipid levels. On the basis of the discussion above, there still remains a need for making a single product that evenly dispenses from routine packaging, therein satisfying the consumers demands for cleansing and skin conditioning.

BACKGROUND ART

The following references relate to multiple liquid phase packaging: U.S. Pat. No. 4,159,028, issued Jun. 26, 1979, in the name of Barker et al.: U.S. Pat. No. 4,335,103, issued Jun. 15, 1982, in the name of Barker et al.; U.S. Pat. No. 6,245,344, issued Jun. 12, 2001 in the name of Thibiant et al.; U.S. Pat. No. 6,367,519, issued Apr. 9, 2002, in the name of Thibiant et al.; U.S. Pat. No. 6,516,838, issued Feb. 11, 2003, in the name of Thibiant et al.

SUMMARY OF THE INVENTION

Figure 1:
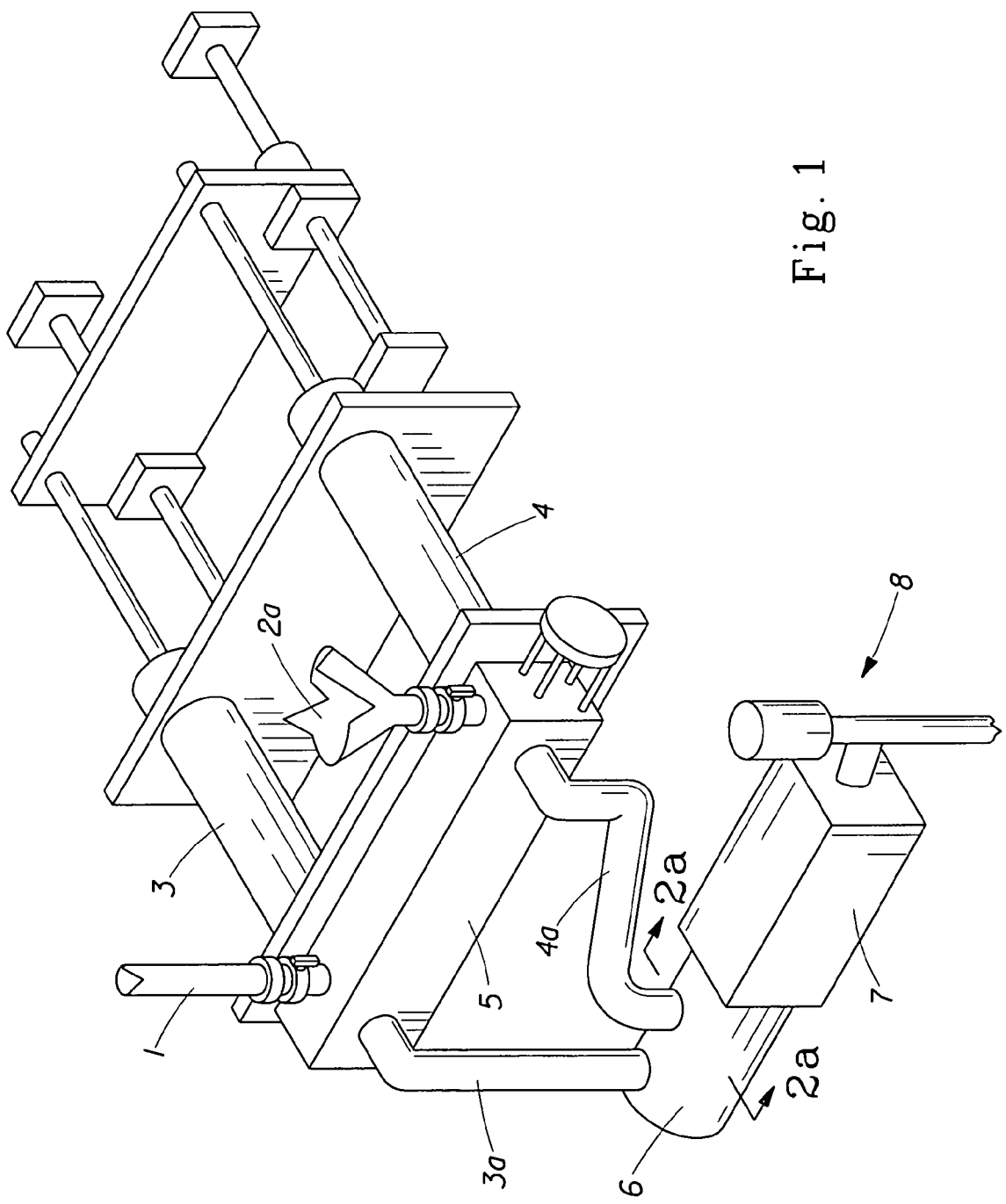
FIG. 1 illustrates a perspective view of an apparatus for making a multiple liquid phase compositions according to an embodiment of the present invention.

The invention relates to a composition comprising a plurality of visually distinctive phases where the phases are processed in such a manner that upon dispensing from a container said composition comprises a designated volume ratio of each phase of the composition. In one particular embodiment of the present invention, upon discharge, the composition contains about equal amounts of each phase as found in the composition in its container.

The invention further relates to a method of making multiple liquid phase compositions, which when dispensed, are distributed in their containers such that consistent doses of each phase are expelled from the container at each dispensing event. Additionally, the designated volume ratio at dispensing from a container is essentially equal to the volume ratio of the phases at the initiation of the process.

The present invention further relates to a process for making multiple liquid phase compositions comprising the steps of:
a) placing a plurality of liquid compositions in separate vessels equipped with means for transferring said compositions from said vessels;
b) transferring predetermined amounts of selected liquid compositions to a combiner;
c) transferring said liquid compositions from said combiner to a blender;
d) blending said liquid composition phases together to produce a combination product wherein said liquid compositions that comprise said combination product are physically distinct from one another; and
e) transferring said combination product through a dispensing means for filling an empty product container;

In an embodiment of this process, the pattern comprises phases that are visually distinct from each other and facilitate even distribution when dispensed.

In one embodiment, this process further involves initially placing the nozzle near the bottom of the container to be filled and lifting the nozzle as the container fills. Additionally, during filling, the container can be secured on a rotating platform for rotating the bottle while being filled. The platform can be rotated at speeds to provide an appropriate pattern of the composition to provide the dispensing benefit mentioned above. Typical platform speeds range from about 0 revolutions per minute (rmp) to 800 rmp. If desired, the rotating platform can be rotated by a variable speed drive mechanism.

The visual distinction between the phases can be in color or texture. The specific pattern can be chosen from a wide variety of patterns, including, but not limited to striping, marbling, geometrics, spirals, and mixtures thereof.

Definitions

The term "ambient conditions" as used herein, unless otherwise specified, refers to surrounding conditions at one (1) atmosphere of pressure, 50% relative humidity, and 25° C.

The term "stable" as used herein, unless otherwise specified, refers to compositions that maintain in visually distinctive phases in physical contact at ambient conditions for a period of at least about 180 days.

The term "personal cleansing composition" as used herein, unless otherwise specified, refers to the compositions of the present invention, wherein the compositions are intended to include compositions for topical application to the skin or hair. In some embodiments personal cleansing compositions comprise a lathering phase and a non-lathering phase.

The term "phase" as used herein refers to a homogeneous, physically distinct, and mechanically separable portion of matter present in a non-homogeneous physical-chemical system. In some embodiments, the phases herein are compositions with different colors. In some embodiments, the phases comprise the same chemical compositions but with different colorants.

The term "lathering" as used herein refers to compositions which, when tested using the Total Lather Volume Method disclosed herein, yield lather volumes of greater than 350 ml.

The term "non-lathering" as used herein refers to compositions which, when tested using the Total Lather Volume Method disclosed herein, yield lather volumes of less than 350 ml.

The term "liquid" as used herein refers to liquid, semi-liquid, cream, lotion or gel compositions, i.e., flowable compositions.

The term "visually distinctive" as used herein describes compositions in the package or upon being dispensed that display visually different phases. These different phases are either distinctively separate or partially mixed as long as the multiple liquid phase composition remains visible to the naked eye.

The term "stripe" as used herein means that each phase present in the composition occupies separate but distinct physical spaces inside the package in which it is stored, but are in direct contact with one another. In one preferred embodiment of the present invention, a personal cleansing composition comprises a lathering phase and a non-lathering that are present within the container as distinct layers or "stripes". The stripes may be relatively uniform and even across the dimension of the package. Alternatively the layers may be uneven, i.e. wavy, or may be non-uniform in dimension. The stripes do not necessarily extend across the entire dimension of the package. The "stripe" can comprise various geometric patterns, various colors and, or glitter or pearlescence, providing that the concentration of said alternative forms visually distinct bands or regions.

The term "marbling" as used herein refers to a striped design with a veined and/or mottled appearance similar to marble.

The methods defined below allow quantitative measurement of the striped and marbled patterns utilized in the compositions comprising multiple liquid phases of the instant application:

1. Method for Measuring Average Stripe Size (AS)

First, a vertical line is drawn along the center of the product package using a pencil. Total the number of visually distinctive product stripes or N, including all product stripes with varying colors. Divide the height of the product package is measured as D in millimeters mm) by N. The average stripe size is calculated as:

$$AS=D/N$$

The average stripe size (AS) in the present invention is about 0.1 mm to about 10 mm. More preferably, the average stripe size is about 0.5 mm to about 5 mm. Most preferably, the average stripe size is about 0.5 mm to about 2 mm.

2. Color Method for Striped/Marbled Multiple Liquid Phase Compositions

The GretagMacbeth Color-Eye 70000A spectrophotometer is used to measure color difference of striped/marbled multiple liquid phase compositions. The aperture size is 3 mm by 8 mm (Very Small Area of View). The instrument is running at reflectance mode with $2^0$ incident light beam. First, one color measurement is made around the lightest area of the sample. This reading is used as the color standard. A second color measurement is made around the darkest area of the sample. This color reading is compared to the color standard (light spot) and color difference is computed as $\Delta E$.

The striped/marbled multiple liquid phase compositions in the present invention have $\Delta E \geq 1$. Preferably, $\Delta E$ is greater than 2. Most preferably, $\Delta E$ is greater than 4.

The methods defined in the following paragraphs are methods for measuring the volume of each phase as a ratio of one to another in terms of the composition dispensed from the container. Multiple liquid phase compositions of the present invention deliver a consistent ratio of the all phases of the composition when dispensed from the container.

1) Ultracentrifugation Method for Multiple Liquid Phase Compositions with Different Densities.

A Beckman LM-8 Ultracentrifuge is used to determine dispensing ratio of multiple liquid phase composition with different densities. The determination is determined at 50 C at 50,000 rpm for one hour using the SW 60Ti rotor. The dispensing ratio between the multiple phases can be determined through the phase volume measurement after ultracentrifugation.

2) Color Method for Multiple Liquid Phase Compositions with Varying Colors.

A GretagMacbeth Color-Eye 70000A spectrophotometer is used to determine dispensing ratio of multiple liquid phase compositions with different colors. First, prepare a set of standard color samples by mixing different colored phases at various mixing ratios. Gently mixing the samples to make sure the samples are homogeneous. Then, take the color measurements using the color instrument and record the color readings. Then, dispense product from the package at about 10 grams interval. Gently mix these dispensed samples and then take the color measurements. The actual dispensing ratio can be determined by comparing the color reading of the dispensed sample closest to the color standard with a known mixing ratio.

3) Chemical Analysis Method

Chemical analysis method is used to determine dispensing ratio of multiple liquid phase products when a chemical compound is used as a marker molecule in one of the multiple liquid phase compositions. By analyzing chemical concentration of the marker molecules through standard analytical method (e.g., GC, LC, and Mass Spectrometry), the dispensing ratio can be calculated.

For purposes of the instant disclosure, lather, viscosity and yield point are measured by the methods disclosed below.

Lather Volume Method

Lather volume of a striped liquid personal cleansing composition is measured using a graduated cylinder and a tumbling apparatus. A 1,000 ml graduated cylinder is chosen which is marked in 10 ml increments and has a height of 14.5 inches at the 1,000 ml mark from the inside of its base (for example, Pyrex No. 2982). Distilled water (100 grams at 23° C.) is added to the graduated cylinder. The cylinder is clamped in a rotating device, which clamps the cylinder with an axis of rotation that transects the center of the graduated cylinder. One gram of the total personal cleansing composition is added into the graduated cylinder and the cylinder is capped. The cylinder is rotated at a rate of 10 revolutions in about 20 seconds, and stopped in a vertical position to complete the first rotation sequence. A timer is set to allow 30 seconds for the lather thus generated to drain. After 30 seconds of such drainage, the first lather volume is measured to the nearest 10 ml mark by recording the lather height in ml up from the base (including any water that has drained to the bottom on top of which the lather is floating).

If the top surface of the lather is uneven, the lowest height at which it is possible to see halfway across the graduated cylinder is the first lather volume (ml). If the lather is so coarse that a single or only a few foam cells ("bubbles") reach across the entire cylinder, the height at which at least 10 foam cells are required to fill the space is the first lather volume, also in ml up from the base. Foam cells larger than one inch in any dimension, no matter where they occur, are designated as unfilled air instead of lather. Foam that collects on the top of the graduated cylinder but does not drain is also incorporated in the measurement if the foam on the top is in its own continuous layer, by adding the ml of foam collected there using a ruler to measure thickness of the layer, to the ml of foam measured up from the base. The maximum foam height is 1,000 ml (even if the total foam height exceeds the 1,000 ml mark on the graduated cylinder). One minute after the first rotation is completed, a second rotation sequence is commenced which is identical in speed and duration to the first rotation sequence. The second lather volume is recorded in the same manner as the first, after the same 30 seconds of drainage time. A third sequence is completed and the third lather volume is measured in the same manner, with the same pause between each for drainage and taking the measurement.

The lather result after each sequence is added together and the Total Lather Volume determined as the sum of the three measurements, in ml. The Flash Lather Volume is the result after the first rotation sequence only, in ml, i.e., the first lather volume. The lathering cleansing compositions of the present invention have Total Lather Volume greater than 400 ml and Flash Lather Volume greater than 150 ml.

Viscosity of the Liquid Personal Cleansing Composition

The Wells-Brookfield Cone/Plate Model DV-II+ Viscometer is used to determine the viscosity of the liquid personal cleansing compositions herein. The determination is performed at 25 C with the 2.4 cm$^0$ cone measuring system with a gap of 0.013 mm between the two small pins on the respective cone and plate. The measurement is performed by injecting 0.5 ml of the sample to be analyzed between the cone and plate and toating the cone at a set speed of 1 rpm. The resistance to the rotation of the cone produces a torque that is proportional to the shear stress of the liquid sample. The amount of torque is read 2 minutes after loading the sample and computed by the viscometer into absolute centipoise units (mPa*s) based on the geometric constant of the cone, the rate of rotation, and the stress related torque.

The viscosity of the compositions disclosed herein ranges from 2,000 to 100,000 centipoise. Preferably, the viscosity is between 5,000 and 60,000 centipoise.

Yield Point of Liquid Personal Cleansing Composition

The Carrimed CSL 100 Controlled Stress Rheometer is used to determine the yield point of the liquid personal cleansing compositions. For purpose herein, the yield point is the amount of stress required to produce a strain of 1% on the liquid personal cleansing composition. The determination is performed at 77 F with the 4 cm 2$^0$ cone measuring system set with a 51 micron gap. The determination is performed via the programmed application of a shear stress (typically from about 0.06 dynes/sq. centimeter to about 500 dynes/sq. centimeter) over time interval of 5 minutes. It this amount of stress results in a deformation of the sample, a shear stress vs. strain curve can be created. From this curve, the yield point of the liquid personal cleansing composition can be calculated. Multiple liquid phase compositions as disclosed herein have values greater than 0.5 Pascal.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

DETAILED DESCRIPTION OF THE INVENTION

As stated above, the invention relates to compositions with multiple liquid phases and a process for making such compositions. These compositions are easily dispensed from their containers such that consistent doses of each phase are expelled from the container at each dispensing event. In addition, to the cleansing performance and even application/distribution of skin conditioning agents or skin actives provided by the instant multiple liquid phase products, the instant personal cleansing composition embodiments allow consumers to utilize the entire contents of the container even the last dose administered will comprise all phases of the combination product.

Surprisingly, in instances where the mixing element of the blender is present, doses of a typical lathering phase to non-lathering phase demonstrate volume ratios which average 50:50 with no values outside the range of 40:60 to 60:40. Where the mixing element of the blender was not present a wide range of dispensing ratios from 0:100 to 100:0 are obtained.

While many variations in the physical characteristics of the components are possible, i.e., color, rheology, texture, density etc, variations in color are widely sought. The specific design or pattern achieved (i.e., width, length of stripe or marbling etc.) in the combination product can be varied by varying a number of factors including, but not limited to rheological characteristics of the phases, diameter of the dispensing means, presence or absence of rotation of the container during filling, rate of speed and constancy.

Placement of the dispensing means during filling of these multiple liquid phase products is an additional process variable. In one embodiment, the process involves initially placing the nozzle near the bottom of the container to be filled and lifting the dispensing means as the container fills. In other variations, the container itself can be raised on the dispensing means, or the container can be filled from the top. In one possible variation, the container can be filled upside down and the bottom attached to the container following filling.

For embodiments where a non-lathering (lipid) phase is utilized, the lathering phase may require heating and passing through a heat exchanger for cooling prior to start of the combining/filling process.

In one embodiment of the invention the composition is dispensed from the container upon being hand squeezed or inverted to gravity feed the composition. In one embodiment, the process is used to produce a spirally striped personal cleansing composition having a first stripe comprising a lathering phase containing a surfactant, water, and optional conventional personal cleansing ingredients and at least one additional stripe comprising a separate non-lathering phase Personal cleansing compositions have now been formulated which allow both a lathering phase (cleansing) and a non-lathering phase which can comprise a variety of phase types including but not limited to water in oil, continuous oil or high internal phase emulsion phases to be packaged in physical contact while remaining stable for prolonged periods. Further, one or more of the phases can include stable colorants, resulting in the possibility of visual patterns when the personal cleansing compositions are packaged in containers which allow the contents to be viewed.

These multiple liquid phase personal cleansing compositions comprise lathering and non-lathering phases that are processed so that the two separate phases are in physical contact yet remain stable. The compositions provide improved deposition of conditioning agents on skin. Skin conditioners applied to the body via the instant multiple liquid phase compositions deposit evenly, and impart excellent skin feel benefits.

These compositions further provide improved cosmetics via the striped appearance and improved skin feel during and after application. It has been found that such compositions with one or more separate phases in physical contact can be formulated with sufficiently high levels of benefit agents without compromising product lather performance and stability. The superior lather performance can be demonstrated via the lather volume method described herein.

It has also been found that the striped personal cleansing compositions can be formulated with selected skin active agents that provide improved chronic skin benefits to the skin. These compositions comprise a lathering phase containing a cleansing surfactant and at least one additional separate phase containing a skin active agent, wherein the cleansing and active phases are packaged in physical contact while remaining stable for long periods of time. Skin active agents appropriate for use in the compositions of the instant invention comprise, but are not limited to vitamins and derivatives thereof; sunscreens; anti-acne medicaments; antioxidants; skin soothing and healing; chelators and sequestrants; essential oils, skin sensates, pigments, pearlescent agents, lakes, colorings, and mixtures thereof. Colorants useful in the present invention are selected from the group consisting of Red 30 Low Iron, FD&C Red 40 AL Lake, D&C Red Lake Blend of Lake 27 & Lake 30, FD&C Yellow 5 Al Lake, FD&C Yellow 6 Al Lake, FD&C Yellow 5 Lake, FD&C Blue #1 AL Lake, Kowet Titanium Dioxide, D&C Red 30 Talc Lake, D&C Red 6 Barium Lake, D&C Red 7 Calcium Lake, D&C Red 34 Calcium Lake, D&C Red 30 AL lake, D&C Red 27 AL lake, D&C Yellow 10 AL lake, D&C Red 21 AL Lake, Yellow Iron Oxide, D&C Red 30 Lake, Octocir Yellow 6 AL Lake, Octocir Yellow 5 AL Lake, D&C Red 28 Lake, D&C Orange 5 Zirc Al Lake, Cos Red Oxide BC, Cos Iron Oxide Red BC, Cos Iron oxide Black BC, Cos Iron Oxide Yellow, Cos Iron Oxide Brown, Cos Iron Oxide Yellow BC, Euroxide Red Unsteril, Euroxide Black Unsteril, Euroxide Yellow Steril, Euroxide Black Steril, Euroxide Red, Euroxide Black, Hydrophobic Euroxide Black, Hydrophobic Euroxide Yellow, Hydrophobic Euroxide Red, D&C Yellow 6 Lake, D&C Yellow 5 Zr Lake, and mixtures thereof.

FIG. 1 illustrates a perspective view of one embodiment of the parts used to make the multiple liquid phase compositions of the present invention and fill the packaging into which it will be sold. This figure represents a single filling station. On a manufacturing scale this alignment of equipment as shown in FIG. 2 is repeated for as many filling stations as is desired for simultaneously filling of a plurality of containers. Connecting or supply lines 1 and 2a are in communication with each phase's supply vessel, not illustrated herein. Said supply lines 1 and 2a can be in the form of hard or flexible piping such as stainless pipes or hoses, useful in transporting said phases from their respective supply vessels. Such supply vessels are typically stainless steel and are equipped with valves at their base wherein flow can be shut off to allow for changing such vessels without shutting down the processing equipment. Said supply lines may be equipped with an inline pump from the supply vessel, thereby pressurizing the supply line to ensure consistent or steady flow from its connected supply vessel. FIG. 1 illustrates a situation wherein supply line 1 is hard plumbed with an in-line pump not shown, whereas supply line 2a is not under pressure and the respective liquid phase feeds from the supply vessel into the funnel shown therein. Supply lines 1 and 2a lead to valves 5 that regulate flow of each phase to its respective pump, in this illustration, pumps 3 and 4. In FIG. 1 the pumps are illustrated as positive displacement, piston-type cylinders. Valves 5 are rotary valves that open to allow the flow of each phase from its supply vessel to enter the pump's cylinder as the pump piston is in its back or down stroke. There is a single valve for each pump and all the valves act in unison due to their being linked in a manner wherein one drive mechanism actuates all the valves. Alternately, separate drive mechanisms can be used to achieve a similar effect. Simultaneously to the flow entering the piston cylinders, valves 5 close the outlet of said cylinders to prohibit the phase from flowing directly into supply lines 3a and 4a going to combiner 6. Upon the pumps forward or upstroke, valves 5 reverse position, allowing the contents of each pump cylinder to discharge its contents into the direction of the combiner 6 through supply lines 3a and 4a while prohibiting back flow into the vessel supply lines 1 and 2a. Pumps 3 and 4 are used to insure a constant supply of each phase to the combiner section 6. Given the proper flow character of the phase, such piston type pumps may be eliminated. When pumps are utilized, it is preferable that said pumps work in tandem with flow meters to insure consistent flow by the pump. Not illustrated herein, volumetric flow meters, and, or mass flow meters that can be utilized to adjust the pumps to insure constant flow. This can also be accomplished by utilizing metering type pumps to deliver the required volume or mass of each phase.

Prior to the phases entering the blender 7, the supply lines 3a and 4a are aligned in such a manner as shown in the cross-sectional views of FIG. 2 in the combiner section 6.

Figure 2A:
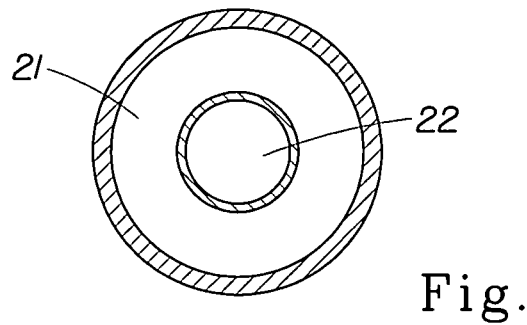
FIG. 2a-c illustrate cross-sectional views of typical blender inlet sections used to produce the multiple liquid phase compositions of the present invention.
Figure 2B:
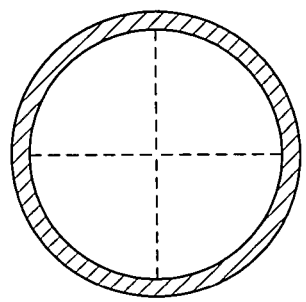
Figure 2C:
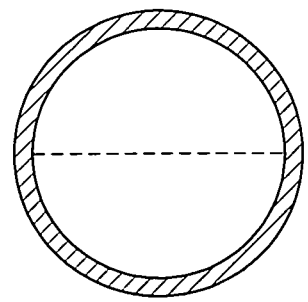

FIG. 2 represents a cross-sectional view of the alignment of the phase feeds from line 3a and 4a as they are prepared for entering blender 7. FIG. 2a illustrates an alignment of feeds from 3a and 4a wherein independent feed line 21 is located within feed line 22, thereby injecting the phase coming from 21 into the center of the feed from line 22 prior to going into the blender 7. FIG. 2c is an alternative to FIG. 2a where the feeds are aligned side by side in a common line from the combiner section 6. FIG. 2b similarly illustrates the situation where four feeds are combined together in one line coming from the combiner section 6 going to blender 7. As an alternative, 2b and 2c, a bundle of piping running parallel representing multiple feeds could also be used.

After moving through the combiner section 6, the aligned phases are introduced into a blending section 7. The blender section 7 comprises a mixing element that comprises a series of obstructions for diverting the liquid phases entering, inducing turbulence and causing the phases to blend together in a way that contributes to forming the composition's eventual in-package pattern. In most cases a static mixer is utilized in the blending section. Static mixers are well know in the art and are generally in the form of a series of repeating or random, interlocking plates and, or fins. Static mixers suitable for use in the process are the Chemineer SSC.75-4R-S (KMA 4 element ¾") available from Chemineer Inc. P.O. Box 1123, Dayton, Ohio 45401 and the Koch SMX 4 element mixer (¾" nominal) available from Koch-Glitsch LP Mass Transfer Sales and Engineering, 9525 Kenwood Road, Suite 16-246, Cincinnati, Ohio 45242.

Figure 3:
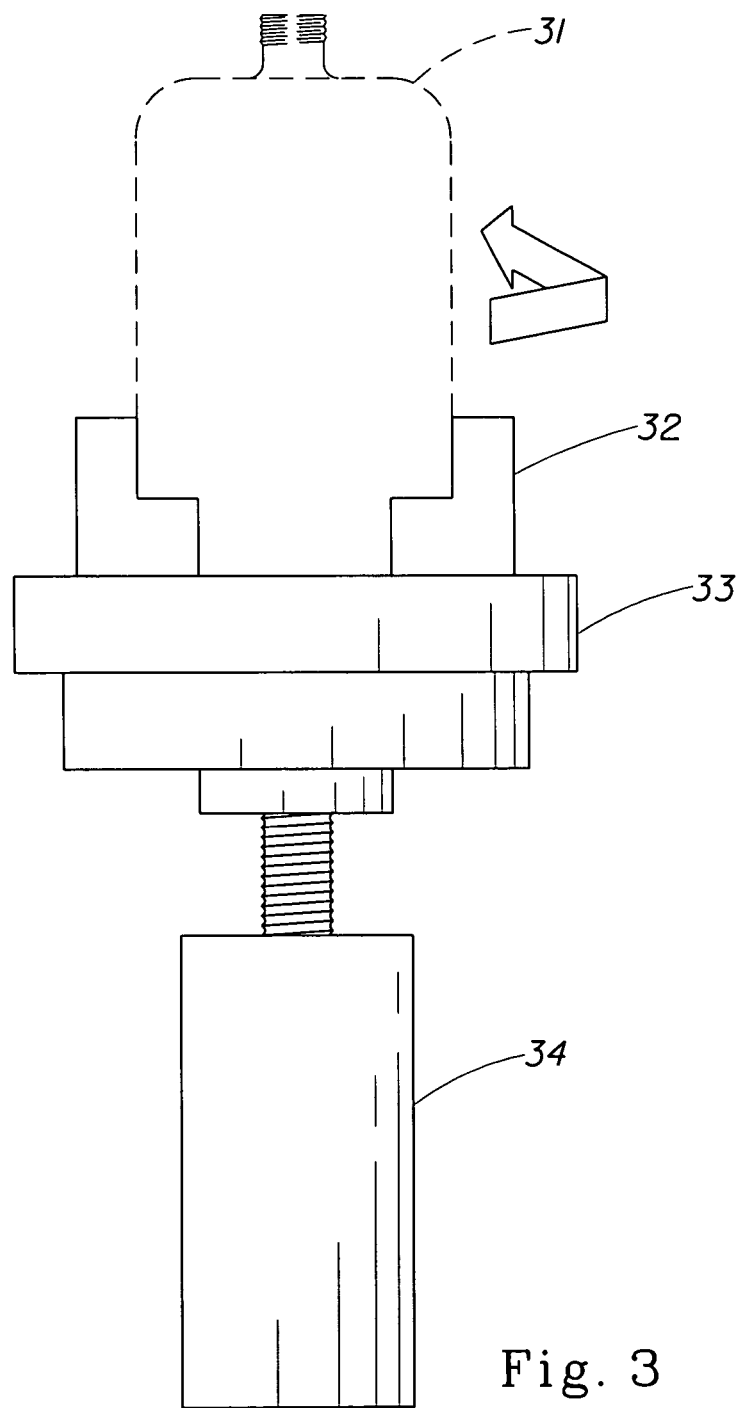
FIG. 3 illustrates a front view of an apparatus for rotation of containers during filling.

After the blended phases pass through blender section 7, the phases are introduced to the delivery nozzle 8. Delivery nozzle 8 is utilized to deliver the combined phases to the bottle. As previously mentioned, in normal manufacturing operations, a plurality of containers will be filled simultaneously. FIG. 3 represents one of a plurality of stations on such equipment. Container 31 is secured into a puck or bottle holder 32. A rotating platform 33 turns the container 31 at a speed determined by the drive mechanism 34. The drive mechanism 34 for the platform 33 can be a variable speed mechanism or a constant speed mechanism. Container 31 is any suitable container for the product. Preferable containers are transparent PET bottles wherein the pattern of the finished composition is visible to the consumer.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

Each of the exemplified compositions provides improved deposition or effectiveness of the skin conditioning agents or optional ingredients delivered from each prepared composition.

Examples 1-3

The following examples described in Table 1 are non-limiting examples of the personal cleaning compositions herein.

TABLE 1

Lathering Phase and Non-lathering (Oil Continuous Conditioning) Phase Compositions

| Ingredient | Example 1 wt % | Example 2 wt % | Example 3 Wt % |
| --- | --- | --- | --- |
| I. Lathering Phase Composition | | | |
| Miracare SLB-365 (from Rhodia) (Sodium Trideceth Sulfate, Sodium Lauramphoacetate, Cocamide MEA) | 47.4 | 47.4 | 47.4 |
| Guar Hydroxypropyltrimonium Chloride (N-Hance 3196 from Aqualon) | 0.7 | 0.7 | 0.7 |
| PEG 90M (Polyox WSR 301 from Dow Chemical) | 0.2 | 0.2 | 0.2 |
| Cocamide MEA | 3.0 | — | — |
| Glycerin | 0.6 | 0.6 | 0.6 |
| Sodium Chloride | 3.5 | 3.5 | 3.5 |
| Disodium EDTA | 0.05 | 0.05 | 0.05 |
| Glydant | 0.67 | 0.67 | 0.67 |
| Citric Acid | 0.4 | 0.4 | 0.4 |
| Expancel 091 DE 40 d30 (from Expancel, Inc.) | 0.4 | 0.4 | 0.4 |
| Perfume | 2.0 | 2.0 | 2.0 |
| Water (pH) | Q.S. (6.0) | Q.S. (6.0) | Q.S. (6.0) |
| II. Conditioning Phase Composition non-lathering | | | |
| Petrolatum (Super White ProtoPet from WITCO) | 75 | 60 | 50 |
| Mineral Oil (Hydrobrite 1000 White Mineral Oil from WITCO) | 24.997 | 39.997 | 49.997 |
| Red 30 Lake | 0.003 | 0.003 | 0.003 |

The compositions described above can be prepared by conventional formulation and mixing techniques. Prepare the lathering phase composition by adding citric acid into water at 1:1 ratios to form a citric acid premix A. Add Polyox WSR 301 into Glycerin and form a premix B. Add the following ingredients into the main mixing vessel in the following sequence: water, N-Hance 3196, Expancel, Citric Acid Premix A, Polyox Premix B. Mix until homogeneous. Then, add the following ingredients: Disodium EDTA, Cocamide MEA, Miracare SLB-365, Sodium Chloride, Glydant, and Perfume. Keep mixing until homogeneous.

The non-lathering (conditioning) phase can be prepared by adding Petrolatum into the main mixing vessel. Then, the vessel is heated to 85 C. Add Hydrobrite Mineral Oil into the main vessel. Then, add Red 30 Lake. Keep mixing until a homogeneous solution forms.

A dual phase piston filler (REB Inc., 5408 3M Drive, Suite A, Menomonie, Wis. 54757 model DV0210) modified to include a combining and blending section and a bottle holding stand that lowers and rotates the bottle during filling is used. Place the cleansing phase into a gravity feed supply container connected the supply inlet on the piston pump for phase 1. Establish a recirculating loop from the heated conditioning phase vessel through a scrape-wall heat exchanger, then through a plate and frame heat exchanger and back to the heated conditioning phase vessel using a positive displacement pump to control the flowrate. Use the scrap wall heat exchanger to cool down the conditioning phase to about 40 C, and set the plate and frame heat exchanger to heat the material back up to about 65 C returning to the heated conditioning phase vessel. Connect the supply inlet of the piston pump for phase 2 to a point between the scrape-wall heat exchanger and the plate and frame heat exchanger, such that there is a supply temperature of about 40 C supplying the pump for phase 2. Use pistons of suitable diameter and length to pump both the cleansing phase and conditioning phase in predetermined amounts (for example 50:50 or 70:30 volume ratio). The piston pumps on the filler will pump the 2 phases through a combining section, blending section, and through the fill nozzle supplying the bottle. The combining section should be set to combine the two phases in a side-by-side manner. The blending section contains a ½" 4 element Koch SMX static Mixer (Koch-Glitsch LP Mass Transfer Sales and Engineering 9525 Kenwood Road Suite 16-246 Cincinnati, Ohio 45242). The mix of phases exiting the nozzle results in a product that exhibits a distinct pattern of the phases. The bottle is raised such that the nozzle starts in a position at the bottom of the bottle and the bottle is lowered as it is filled to keep the nozzle just above the surface of the two phases. A rotating platform spins the bottle during the filling process to create a striped appearance. The platform should be set to rotate at about 250 rpm to create the desired pattern.

Examples 4-6

The following examples described in Table 2 are non-limiting examples of the personal cleaning compositions herein.

TABLE 2

Lathering Phase and Non-lathering(Water in oil) Phase Compositions

| Ingredient | Example 4 wt % | Example 5 wt % | Example 6 wt % |
|---|---|---|---|
| I. Lathering Phase Composition | | | |
| Miracare SLB-365 (from Rhodia) (Sodium Trideceth Sulfate, Sodium Lauramphoacetate, Cocamide MEA) | 47.4 | 47.4 | 47.4 |
| Guar Hydroxypropyltrimonium Chloride (N-Hance 3196 from Aqualon) | — | — | 0.7 |
| PEG 90M (Polyox WSR 301 from Dow Chemical) | — | — | 0.2 |
| Cocamide MEA | 3.0 | — | — |
| Polycare 133 | — | — | 0.4 |
| Lauric Acid | — | 2.0 | 2.0 |
| Sodium Chloride | 3.5 | 3.5 | 3.5 |
| Disodium EDTA | 0.05 | 0.05 | 0.05 |
| Glycerin | 0.6 | 0.6 | 0.6 |
| Glydant | 0.67 | 0.67 | 0.67 |
| Citric Acid | 0.4 | 0.4 | 0.4 |
| Perfume | 2.0 | 2.0 | 2.0 |
| Red 30 Lake | 0.01 | 0.01 | 0.01 |
| Water | Q.S. | Q.S. | Q.S. |
| (pH) | (6.0) | (6.0) | (6.0) |
| II. Water in oil phase Composition | | | |
| Petrolatum | 80 | 80 | 80 |
| PEG-30 Dipolyhydroxystearate (Arlacel P135) | 1 | 1 | 1 |
| Water | 19 | 19 | 19 |

The compositions described above can be prepared by conventional formulation and mixing techniques. Prepare the lathering phase composition by adding citric acid into water at 1:1 ratios to form a citric acid premix A. Add Polyox WSR 301 into Glycerin and form a premix B. Add the following ingredients into the main mixing vessel in the following sequence: water, N-Hance 3196, Expancel, Citric Acid Premix A, Polyox Premix B. Mix until homogeneous. Then, add the following ingredients: Disodium EDTA, Cocamide MEA, Miracare SLB-365, Lauric Acid, Polycare 133, Sodium Chloride, Glydant, Red 30 Lake and Perfume. Keep mixing until homogeneous.

Water in Oil Phase

The non-lathering (water in oil) phase can be prepared by adding Petrolatum into the main mixing vessel. Then, the vessel is heated to 185 F and add Arlacel P135. Then, slowly add water with agitation. The non-lathering (water-in-oil) phase will be kept agitating for one hour. Then, pump the product thoroughly a high shear mixer into a storage tank. Then, the water-in-oil phase cools down to ambient temperate.

A dual phase piston filler (REB Inc., 5408 3M Drive, Suite A, Menomonie, Wis. 54757 model DV0210) modified to include a combining and blending section and a bottle holding stand that lowers and rotates the bottle during filling is used. Place the cleansing phase into a gravity feed supply container connected the supply inlet on the piston pump for phase 1. Place the conditioning phase into a gravity feed supply container connected the supply inlet on the piston pump for phase 2. Use pistons of suitable diameter and length to pump both the cleansing phase and conditioning phase in predetermined amounts (for example 50:50 or 70:30 volume ratio). The piston pumps on the filler will pump the 2 phases through a combining section, blending section, and through the fill nozzle supplying the bottle. The combining section should be set to combine the two phases in a side-by-side manner. The blending section contains a ½" 4 element Koch SMX static Mixer (Koch-Glitsch LP Mass Transfer Sales and Engineering 9525 Kenwood Road Suite 16-246 Cincinnati, Ohio 45242). The mix of phases exiting the nozzle results in a product that exhibits a distinct pattern of the phases. The bottle is raised such that the nozzle starts in a position at the bottom of the bottle and the bottle is lowered as it is filled to keep the nozzle just above the surface of the two phases. A rotating platform spins the bottle during the filling process to create a striped appearance. The platform should be set to rotate at about 250 rpm to create the desired pattern.

Examples 7-9

The following examples described in Table 3 are non-limiting examples of the personal cleansing compositions herein.

TABLE 3

Lathering Phase and Non-lathering (High Internal Phase Emulsion) Phase Compositions

| Ingredient | Example 7 wt % | Example 8 wt % | Example 9 wt % |
|---|---|---|---|
| I. Lathering Phase Composition | | | |
| Ammonium Laureth-3 Sulfate | 3.0 | 3.0 | 3.0 |
| Sodium Lauroamphoacetate (Miranol L-32 Ultra from Rhodia) | 16.7 | 16.7 | 16.7 |
| Ammonium Lauryl Sulfate | 1.0 | 1.0 | 1.0 |
| Lauric Acid | 0.9 | 0.9 | 0.9 |
| Trihydroxystearin (Thixcin R) | 2.0 | 2.0 | 2.0 |
| Guar Hydroxypropyltrimonium Chloride (N-Hance 3196 from Aqualon) | 0.17 | 0.75 | 0.75 |
| Guar Hydroxypropyltrimonium Chloride (Jaguar C-17 from Rhodia) | 0.58 | — | — |

TABLE 3-continued

Lathering Phase and Non-lathering (High Internal Phase Emulsion) Phase Compositions

| Ingredient | Example 7 wt % | Example 8 wt % | Example 9 wt % |
| --- | --- | --- | --- |
| Polyquaterium 10 (UCARE polymer JR-30M from Amerchol) | 0.45 | — | — |
| Polymethacrylamidopropyltrimonium Chloride (Polycare 133 from Rhodia) | — | 0.24 | — |
| Polyquaternium-39 (Merqrut Plus 3300 from Calgon) | — | 0.81 | — |
| PEG 90M (Polyox WSR 301 from Union Carbide) | 0.25 | — | — |
| PEG-14M (Polyox WSR N-3000 H from Union Carbide) | 0.45 | 2.45 | 2.45 |
| Linoleamidoprypyl PG-Dimonium Chloride Phosphate Dimethicone (Monasil PLN from Uniqema) | — | 1.0 | 4.0 |
| Glycerin | 1.4 | 4.9 | 4.9 |
| Sodium Chloride | 0.3 | 0.3 | 0.3 |
| Sodium Benzoate | 0.25 | 0.25 | 0.25 |
| Disodium EDTA | 0.13 | 0.13 | 0.13 |
| Glydant | 0.37 | 0.37 | 0.37 |
| Citric Acid | 1.6 | 0.95 | 0.95 |
| Titanium Dioxide | 0.5 | 0.5 | 0.5 |
| Perfume | 0.5 | 0.5 | 0.5 |
| Red 30 Lake | 0.01 | 0.01 | 0.01 |
| Water | Q.S. | Q.S. | Q.S. |
| II. HIPE phase Composition-Non-lathering | | | |
| Petrolatum (Superwhite Protopet) | 68 | 68 | 68 |
| Cetyl Hydroxyethylcellulos (Natrosol Plus) | 0.91 | 0.91 | 0.91 |
| Water and Minors | Q.S. | Q.S. | Q.S. |

The lathering phase and non-lathering (high internal phase emulsion) phase compositions described above can be prepared by conventional formulation and mixing techniques. Prepare the cleansing composition 7 by first creating the following premixes: citric acid in water premix at 1:3 ratio, Guar polymer premix with Jaguar C-17 and N-Hance 3196 in water at 1:10 ratio, UCARE premix with JR-30M in water at about 1:30 ratio, and Polyox premix with PEG-90M and PEG-14M in Glycerin at about 1:2 ratio. Then, add the following ingredients into the main mixing vessel: ammonium lauryl sulfate, ammonium laureth-3 sulfate, citric acid premix, Miranol L-32 ultra, sodium chloride, sodium benzoate, disodium EDTA, lauric acid, Thixcin R, Guar premix, UCARE premix, Polyox Premix, and the rest of water. Then one will heat the vessel with agitation until it reaches 190° F. (88° C.). Let it mix for about 10 min. Cool the batch with a cold water bath with slow agitation until it reaches 110° F. (43° C.). Add the following ingredients: Glydant, perfume, Titanium Dioxide. Mix until a homogeneous solution forms.

Prepare the lathering composition 8 by first creating the following premixes: citric acid in water premix at 1:3 ratio, Guar polymer premix with N-Hance 3196 in water at 1:10 ratio, and Polyox premix with PEG-14M in Glycerin at about 1:2 ratio. Then, add the following ingredients into the main mixing vessel: ammonium lauryl sulfate, ammonium laureth-3 sulfate, citric acid premix, Miranol L-32 ultra, sodium chloride, sodium benzoate, disodium EDTA, lauric acid, Thixcin R, Guar premix, Polyox Premix, Polycare 133, Merquat Plus 3300, Monasil PLN, and the rest of water. Then, heat the vessel with agitation until it reaches 190° F. (88° C.). Let it mix for about 10 min. Next, the cool batch with a cold water bath with slow agitation until it reaches 110° F. (43° C.). Finally, add the following ingredients: Glydant, perfume, Titanium Dioxide and mixed until a homogeneous solution forms.

Prepare the lathering composition 9 by first creating the following premixes: citric acid in water premix at 1:3 ratio, Guar polymer premix with N-Hance 3196 in water at 1:10 ratio, and Polyox premix with PEG-14M in Glycerin at about 1:2 ratio. Then, add the following ingredients into the main mixing vessel: ammonium lauryl sulfate, ammonium laureth-3 sulfate, citric acid premix, Miranol L-32 ultra, sodium chloride, sodium benzoate, disodium EDTA, lauric acid, Thixcin R, Guar premix, Polyox Premix, Monasil PLN, and the rest of water. Then heat the vessel with agitation until it reaches 190° F. (88° C.). Mix the vessel contents for about 10 min. Next, cool the batch in a cold water bath with slow agitation until it reaches 110° F. (43° C.). Finally, the following ingredients will be added: Glydant, perfume, Titanium Dioxide and mixed until a homogeneous solution forms.

HIPE Phase

Prepare the non-lathering (HIPE) phase by adding water into the main mixing vessel. Then, heat the vessel to 185 F. Then, slowly add Natrosol Plus with agitation. Keep the HIPE phase agitating for one hour. In a separate vessel, the petrolatum will be heated to 185 F. Slowly add the main mixing vessel petrolatum with good agitation. Then, pump the product through a high shear mixer into a storage container and cool to ambient temperature.

A dual phase piston filler (REB Inc., 5408 3M Drive, Suite A, Menomonie, Wis. 54757 model DV0210) modified to include a combining and blending section and a bottle holding stand that lowers and rotates the bottle during filling is used. Place the cleansing phase into a gravity feed supply container connected the supply inlet on the piston pump for phase 1. Place the conditioning phase into a gravity feed supply container connected the supply inlet on the piston pump for phase 2. Use pistons of suitable diameter and length to pump both the cleansing phase and conditioning phase in predetermined amounts (for example 40:60 or 70:30 volume ratio). The piston pumps on the filler will pump the 2 phases through a combining section, blending section, and through the fill nozzle supplying the bottle. The combining section should be set to combine the two phases in a side-by-side manner. The blending section contains a ½" 4 element Koch SMX static Mixer (Koch-Glitsch LP Mass Transfer Sales and Engineering 9525 Kenwood Road Suite 16-246 Cincinnati, Ohio 45242). The mix of phases exiting the nozzle results in a product that exhibits a distinct pattern of the phases. The bottle is raised such that the nozzle starts in a position at the bottom of the bottle and the bottle is lowered as it is filled to keep the nozzle just above the surface of the two phases. A rotating platform spins the bottle during the filling process to create a striped appearance. The platform should be set to rotate at about 250 rpm to create the desired pattern.

Examples 10-12

Examples 10-12 are described in Table 4. Examples 10-12 are non-limiting examples of the personal cleansing compositions herein.

TABLE 4

Lathering Phase and Non-lathering (HIPE) phase Compositions

| Ingredient | Example 10 wt % | Example 11 wt % | Example 12 wt % |
| --- | --- | --- | --- |
| I. Lathering Phase Composition | | | |
| Miracare SLB-365 (from Rhodia) (Sodium Trideceth Sulfate, Sodium Lauramphoacetate, Cocamide MEA) | 47.4 | 47.4 | 47.4 |
| Guar Hydroxypropyltrimonium Chloride (N-Hance 3196 from Aqualon) | — | — | 0.7 |
| PEG 90M (Polyox WSR 301 from Dow Chemical) | — | — | 0.2 |
| Cocamide MEA | 3.0 | — | — |
| Polycare 133 | — | — | 0.4 |
| Lauric Acid | — | 2.0 | 2.0 |
| Sodium Chloride | 3.5 | 3.5 | 3.5 |
| Disodium EDTA | 0.05 | 0.05 | 0.05 |
| Glydant | 0.67 | 0.67 | 0.67 |
| Glycerin | 0.6 | 0.6 | 0.6 |
| Citric Acid | 0.4 | 0.4 | 0.4 |
| Perfume | 2.0 | 2.0 | 2.0 |
| Water | Q.S. | Q.S. | Q.S. |
| (pH) | (6.0) | (6.0) | (6.0) |
| II. Non-lathering (HIPE) phase Composition | | | |
| Petrolatum (Superwhite Protopet) | 68 | 68 | 68 |
| Cetyl Hydroxyethylcellulos (Natrosol Plus) | 0.91 | 0.91 | 0.91 |
| Water and Minors | Q.S. | Q.S. | Q.S. |

The compositions described above can be prepared by conventional formulation and mixing techniques. Prepare the lathering phase composition by adding citric acid into water at 1:1 ratios to form a citric acid premix A. Add Polyox WSR 301 into Glycerin and form a premix B. Add the following ingredients into the main mixing vessel in the following sequence: water, N-Hance 3196, Expancel, Citric Acid Premix A, Polyox Premix B. Mix until homogeneous. Then, add the following ingredients: Disodium EDTA, Cocamide MEA, Miracare SLB-365, Lauric Acid, Polycare 133, Sodium Chloride, Glydant, Red 30 Lake and Perfume. Keep mixing until homogeneous.
HIPE Phase Prepare the non-lathering (HIPE) phase by adding water into the main mixing vessel. Then, heat the vessel to 185 F. Then, slowly add Natrosol Plus with agitation. Agitate the non-lathering (HIPE) phase for one hour. In a separate vessel, the petrolatum will be heated to 185 F. The main mixing vessel will have petrolatum slowly added with good agitation. Then, pump the product through through a high shear mixer into a storage container and cools to ambient temperature.

A dual phase piston filler (REB Inc., 5408 3M Drive, Suite A, Menomonie, Wis. 54757 model DV0210) modified to include a combining and blending section and a bottle holding stand that lowers and rotates the bottle during filling is used. Place the cleansing phase into a gravity feed supply container connected the supply inlet on the piston pump for phase 1. Place the conditioning phase into a gravity feed supply container connected the supply inlet on the piston pump for phase 2. Use pistons of suitable diameter and length to pump both the cleansing phase and conditioning phase in predetermined amounts (for example 50:50 or 70:30 volume ratio). The piston pumps on the filler will pump the 2 phases through a combining section, blending section, and through the fill nozzle supplying the bottle. The combining section should be set to combine the two phases in a side-by-side manner. The blending section contains a ½" 4 element Koch SMX static Mixer (Koch-Glitsch LP Mass Transfer Sales and Engineering 9525 Kenwood Road Suite 16-246 Cincinnati, Ohio 45242). The mix of phases exiting the nozzle results in a product that exhibits a distinct pattern of the phases. The bottle is raised such that the nozzle starts in a position at the bottom of the bottle and the bottle is lowered as it is filled to keep the nozzle just above the surface of the two phases. A rotating platform spins the bottle during the filling process to create a striped appearance. The platform should be set to rotate at about 250 rpm to create the desired pattern.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for making patterned multi-phase liquid compositions wherein upon dispensing said multi-phase liquid compositions from a container, phases of said multi-phase liquid compositions are dispensed evenly from said container, said process comprising:
    placing a plurality of liquid phases in separate vessels equipped with supply lines for transferring said phases from said vessels;
    transferring, via said supply lines, predetermined amounts of each of said liquid phases from each of said separate vessels into a combiner which aligns each of said liquid phases in at least one of the following: one of said liquid phases is aligned within another of said liquid phases, said liquid phases are aligned side by side along a common line, or said liquid phases are combined into one line;
    transferring said liquid phases from said combiner to a blender;
    blending said liquid phases together, via said blender, to produce a multi-phase liquid composition having equal volume ratios of one phase to another; and
    transferring said multi-phase liquid composition to an individual product container via a delivery nozzle, wherein said individual product container is received at a bottle holding device and secured to a rotating platform attached to said bottle holding device, and wherein said individual product container is rotated, via said rotating platform, when said multi-phase liquid composition is transferred to said individual product container via said delivery nozzle.

2. The process of claim 1 wherein said multi-phase liquid composition has a visually distinctive pattern formed when said liquid phases are blended.

3. The process of claim 1 wherein the rotating platform is rotated between 0 revolutions per minute and 800 revolutions per minute.

4. A process for making patterned multi-phase liquid compositions wherein upon dispensing said multi-phase liquid compositions from a container, phases of said multi-phase liquid compositions are dispensed evenly from said container, said process comprising:
- placing a plurality of physically distinct liquid phases in separate vessels equipped with supply lines for transferring said physically distinct liquid phases from said vessels;
- transferring, via said supply lines, predetermined amounts of each of said physically distinct liquid phases from each of said separate vessels into a combiner which aligns each of said physically distinct liquid phases;
- transferring said physically distinct liquid phases from said combiner to a blender;
- blending said physically distinct liquid phases together, via a mixing element of said blender, to produce a multi-phase liquid composition having a visually distinct pattern formed by said physically distinct liquid phases and equal volume ratios of said physically distinct liquid phases; and
- transferring said multi-phase liquid composition to an individual product container via a delivery nozzle, wherein said individual product container is received at a bottle holding device and secured to a rotating platform attached to said bottle holding device, and wherein said individual product container is rotated, via said rotating platform, when said multi-phase liquid composition is transferred to said individual product container via said delivery nozzle.

5. The process of claim 4 wherein the rotating platform is rotated between 0 revolutions per minute to 800 revolutions per minute.

6. The process of claim 4 wherein said physically distinct liquid phases comprise a lathering phase and a non-lathering phase.

7. The process of claim 4 wherein said individual product container is filled with said multiple liquid phase composition from a bottom of said individual product container.

8. The process of claim 4 wherein said visually distinct patterns are selected from the group consisting of stripes, marbling, geometrics, spirals, and mixtures thereof.

9. The process of claim 2 wherein said visually distinct patterns are selected from the group consisting of stripes, marbling, geometrics, spirals, and mixtures thereof.

10. The process of claim 1 wherein said liquid phases comprise a lathering phase and a non-lathering phase.

11. The process of claim 1 wherein said individual product container is filled with said multiple liquid phase composition from a bottom of said individual product container.

12. A process for making patterned multi-phase liquid compositions, said process comprising:
- placing a plurality of liquid phases in separate vessels equipped with supply lines for transferring said liquid phases from said vessels;
- transferring, via said supply lines, predetermined amounts of each of said liquid phases from each of said separate vessels into a combiner which aligns each of said liquid phases;
- transferring said liquid phases from said combiner to a blender;
- blending said liquid phases together, via a mixing element of said blender, to produce a multi-phase liquid composition having a visually distinct pattern formed by said liquid phases; and
- transferring said multi-phase liquid phase composition to an individual product container via a delivery nozzle, wherein said individual product container is received at a bottle holding device and secured to a rotating platform attached to said bottle holding device, and wherein said individual product container is rotated, via said rotating platform, when said multi-phase liquid composition is transferred to said individual product container via said delivery nozzle.

13. The process of claim 12 wherein the rotating platform is rotated between 0 revolutions per minute to 800 revolutions per minute.

14. The process of claim 12 wherein said individual product container is filled with said multiple liquid phase composition from a bottom of said individual product container.

15. The process of claim 12 wherein said multi-phase liquid composition comprises volume ratios of said liquid phases.

16. The process of claim 15 wherein said volume ratios are in the range of 40:60 to 60:40.

17. The process of claim 12 wherein said visually distinct patterns are selected from the group consisting of stripes, marbling, geometrics, spirals, and mixtures thereof.

18. The process of claim 12 wherein said individual product container is a cylindrical PET bottle with a closure comprising a dispensing orifice.

19. The process of claim 12 wherein said phases comprise a lathering phase and a non-lathering phase.

20. The process of claim 12, wherein said liquid phases are in physical contact when said multiple liquid phase composition is transferred to said individual product container.

* * * * *